United States Patent

Haeck et al.

[11] Patent Number: 5,049,563
[45] Date of Patent: Sep. 17, 1991

[54] ANNELATED INDOLEKETONES WITH AN IMIDAZOLYLALKYL SUBSTITUENT

[75] Inventors: Hans H. Haeck; Derk Hamminga; Ineke van Wijngaarden; Wouter Wouters, all of Weesp, Netherlands

[73] Assignee: Duphar International Research B.V., Netherlands

[21] Appl. No.: 374,774

[22] Filed: Jul. 3, 1989

[30] Foreign Application Priority Data

Jul. 7, 1988 [NL] Netherlands ............... 8801714

[51] Int. Cl.$^5$ ................ A61K 31/435; C07D 221/18
[52] U.S. Cl. ........................... 514/284; 546/71; 540/450; 540/576; 548/420; 514/214; 514/410; 514/183
[58] Field of Search ............ 546/94, 71; 548/428, 548/425; 514/284

[56] References Cited

U.S. PATENT DOCUMENTS 4,716,162 12/1987 Tomita et al. .................. 514/214
4,748,247 5/1988 Abou-Gharbia ............... 548/429
4,822,881 4/1989 Coates et al. .................. 540/603

FOREIGN PATENT DOCUMENTS 297651 6/1987 European Pat. Off. ......... 546/94

Primary Examiner—Jane T. Fan
Assistant Examiner—Celia Chang
Attorney, Agent, or Firm—Stevens, Davis, Miller & Mosher

[57] ABSTRACT

Annelated indoleketones with an imidazolylalkyl substituent having the formula (2):

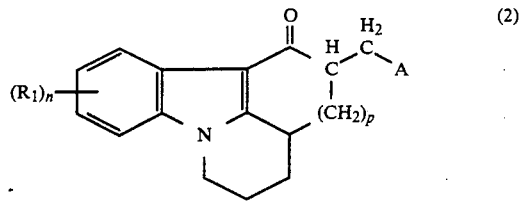

wherein
$R_1$ is alkyl or alkoxy having 1-4 C-atoms, hydroxy, halogen, trifluoromethyl, a group $R_5R_6N$ or $R_5R_6$-N-CO, wherein $R_5$ and $R_6$ are hydrogen or alkyl having 1-4 C-atoms or wherein $R_5R_6N$ is a saturated 5-6 ring, and n has the value 0, 1 or 2;
A is a group of formula 3, 4 or 5

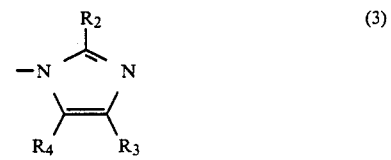

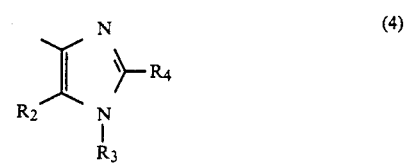

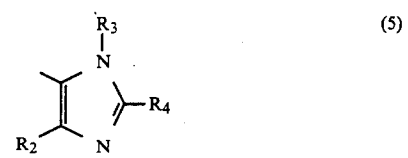

wherein one of the groups $R_2$, $R_3$ and $R_4$ is hydrogen, alkyl having 1-4 C-atoms, cycloalkyl having 3-6 C-atoms or alkenyl having 2-4 C-atoms and the two other groups, independently of each other, are hydrogen or alkyl having 1-4 C-atoms,
p has the value 0-3, and q has the value 2-5. These compounds (and pharmaceutically acceptable acid addition salts thereof) have good antagonistic activity of "neuronal" 5-hydroxytryptamine(5-HT)receptors, and the lower toxicity.

3 Claims, No Drawings

ANNELATED INDOLEKETONES WITH AN IMIDAZOLYLALKYL SUBSTITUENT

The invention relates to a group of new annelated indoleke-tones which comprise at the carbon atom, besides the carbonyl group, an imidazolylalkyl group as a substituent, to the preparation thereof, and to compositions which comprise at least one of these compounds as an active substance.

It is known from Belgian Patent Specification No. 901576 and European Patent Application No. 86305671.9 (publication No. 0210840) that carbazolone compounds of the formula 1:

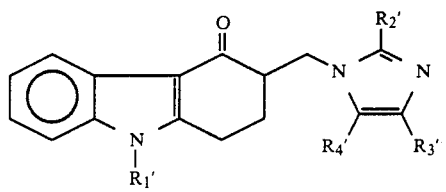

wherein $R'_1$ is hydrogen, alkyl having 1–10 C-atoms, cycloalkyl having 3–7 C-atoms, alkenyl having 3–6 C-atoms, phenyl or pheylalkyl (1–3 C in the alkyl group), and a group $CO_2R'_5$, $COR'_5$, $CONR'_5R'_6$ or $SO_2R'_5$, respectively, (wherein $R'_5$ and $R'_6$ may inter alia be alkyl or cycloalkyl), and wherein one of the groups $R'_2$, $R'_3$ and $R'_4$ is hydrogen, alkyl (1–6 C), cycloalkyl (3–7 C), alkenyl (2–6 C) or phenylalkyl (1–3 C) in the alkyl group, and the two other groups may be hydrogen or alkyl (1–6 C), are strong and selective antagonists of "neuronal" 5-hydroxytryptamine (5-HT) receptors It has now been found surprisingly that compounds of formula 2

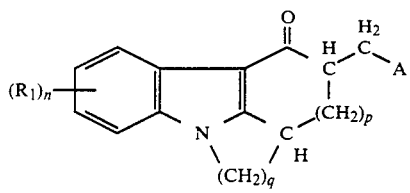

wherein
$R_1$ is alkyl or alkoxy having 1–4 C-atoms, hydroxy, halogen, trifluoromethyl, a group $R_5R_6N$ or $R_5R_6$—N—CO, wherein $R_5$ and $R_6$ are hydrogen or alkyl having 1–4 C-atoms or wherein $R_5R_6N$ is a saturated 5–6 ring, and n has the value 0, 1 or 2;
A is a group of formulae 3, 4 or 5

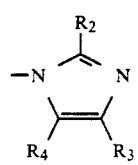

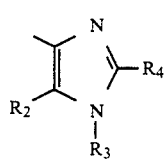

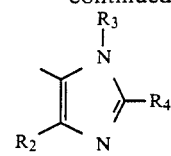

wherein one of the groups $R_2$, $R_3$ and $R_4$ is hydrogen, alkyl having 1–4 C-atoms, cycloalkyl having 3–6 C-atoms or alkenyl having 2–4 C-atoms and the two other groups, independently of each other, are hydrogen or alkyl having 1–4 C-atoms,
p has the value 0–3 and g has the value 2–5 and the pharmaceutically acceptable acid addition salts thereof have a similar but considerably prolonged activity and a lower toxicity than the known compounds of formula 1.

Suitable acids with which the compounds of formula 2 according to the invention can form pharmaceutically acceptable acid addition salts are, for example, hydrochloric acid, sulphuric acid, phosphoric acid nitric acid, and organic acids, for example, citric acid, fumaric acid, maleic acid, tartaric acid, acetic acid, benzoic acid, p-toluene sulphonic acid, methane sulphonic acid, and the like.

The invention includes both the racemates and the individual enantiomers of compounds of formula 2.

The antagonistic activity of the compounds of formula 2 on the response induced by 5-HT was determined and measured in the Bezold-Jarish reflex test in rats. The affinity to "neuronal" 5-HT receptors was determined and measured by the displacement of ($^3$H)GR 38032 F of neuroblastoma cells.

On the basis of the antagonistic activity on this type of 5-HT receptors the compounds may be used for the treatment of symptoms which are caused by overexcitation of the said receptors a) in the gastrointestinal system (nausea and vomiting as a result of exogenic factors, for example, cancer therapy, or endogenic factors, for example, stasis of the stomach and migraine), ulcer, dyspepsia, spasms, irritable bowel syndrome, etc., or b) in the central nervous system (hallucinations, delusions, manias, fear, depressions, pain, improvement of vigilance, nausea, etc., or c) in the cardio-vascular system, for example, spasms of the vessels, arrhytmias, etc., or d) in the respiratory system (including nasal disturbances and disturbances of bronchi and lungs), or e) to alleviate or prevent withdrawal effects induced by abuse of drugs.

The compounds according to the invention and their salts can be brought into forms suitable for administration, for example, pills, tablets, coated tablets, capsules, powders, injection liquids, and the like, by means of techniques conventionally used for this purpose and while using suitable auxiliary substances, for example, solid or liquid carrier materials.

The dosage in which the compounds according to the invention may be used depends on the severity and the nature of the disease to be treated and on the way of administration. As a rule the daily dosage will be between 0.05 and 20 mg, preferably between 0.1 and 10 mg of active substance.

The compounds according to the invention may be prepared in a manner known for analogous compounds. Suitable methods for the preparation of this type of compounds are described, for example, in the above-mentioned European Patent Application published under No. 0210840.

In particular, the compounds of formula 2 wherein A is a group of formula 3 can be obtained in a good yield by a) reaction of a compound of formula 6

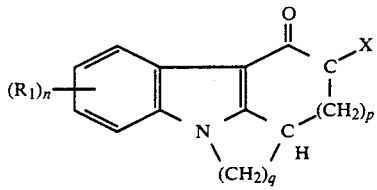

wherein R₁, n, p and g have the above-mentioned meanings, and X is a reactive group, preferably the group —CH₂ or —CH₂N(CH₃)₂, with an imidazole compound of formula 7

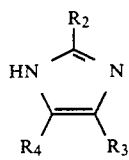

or a salt thereof, wherein R₂, R₃ and R₄ have the above-mentioned meanings.

The reaction is preferably carried out in a suitable solvent, for example, water, alcohol, dimethyl formamide, etc., at temperatures between 20° C. and 150° C.

The starting compounds of formula 6 to be used in this reaction can be obtained, for example, by reaction of a compound of formula 8

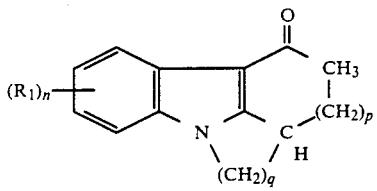

Wherein R₁, n, p and g have the meanings mentioned hereinbefore, with formaldehyde and dimethylamine hydrochloride, preferably in an organic solvent, for example, acetic acid or alcohol, while heating.

The starting substances of formula 8 may be obtained in a manner known per se. for example, by oxidation of a compound of formula 9 or 10

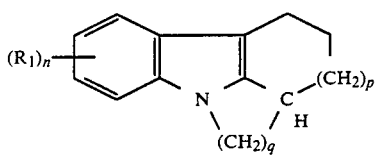

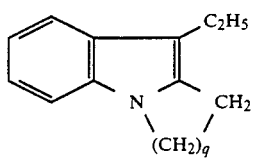

wherein R₁, n, p and g have the meanings mentioned hereinbefore, with a suitable oxidation agent, for example, 2,3-dichloro-5,6-dicyano-1,4-benzoquinone (DDQ) or selenium dioxide, preferably in a suitable solvent, for example water, tetrahydrofuran or dioxan. In particular the starting substances of formula 8 can be obtained in a good yield by oxidation with DDQ of the analogous compounds of formula 9 or 10 in tetrahydrofuran and water at temperatures between −10° and 20° C. as is described for similar compounds in J. Org. Chem. 42, (1977), 1213.

The compounds of formulae 9 and 10 are known compounds or can be obtained analogously to known compounds.

Compounds of formula 2 wherein A is a group of formula 4 or 5, and R₃ and R₄ are hydrogen, can be obtained in good yield by reaction of a compound of formula 6, wherein R₁, n, p and g have the above-mentioned meanings, and X is an alkalimetal atom, with a compound of formulae 11 or 12

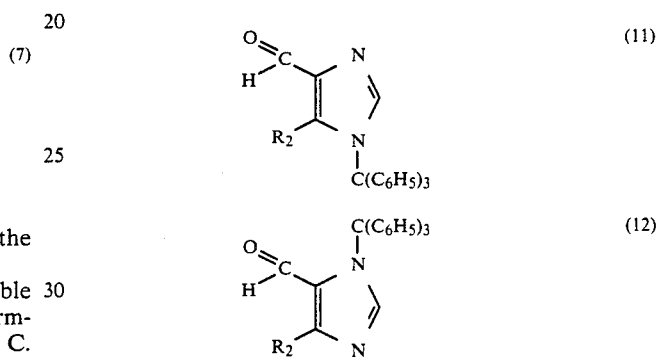

wherein R₂ has the above-mentioned meaning, splitting off water and removing the trityl group under acid conditions from the obtained product, and hydrogenating the so-obtained product, for example with palladium as a catalyst in a suitable solvent.

Compounds of formula 2, wherein A is a group of the formulae 4 or 5 wherein R₁, R₂ R₃ R₄, n, p and g have the meaning mentioned in formula 2, on the understanding that R₃ cannot be hydrogen, can be obtained in good yields by reacting the analogous compounds of formula 2 wherein R₃ is an alkalimetal atom, with a compound R₃—X, wherein X is a group or atom which can be replaced by a nucleophile.

The invention will now be described in greater detail with reference to the ensuing specific examples.

EXAMPLE I a)

2,3,3a,4,5,6-Hexahydro-1H-pyrido[3,2,1-jk]carbazol-1-one 7.2 g (0.034 mol) of 2,3,3a,4,5,6-hexahydro-1H-pyrido[3,2,1-jk]carbazole prepared according to A. S. Baily et al. J. C. S. Perkin I (1980) 97, were dissolved in 300 ml of tetrahydrofuran. The mixture was diluted with 30 ml of water and cooled to 0° C. A solution of 17.0 g (0.075 mol) of 2,3-dichloro-5,6-dicyano-1,4-benzoquinone in 150 ml of tetrahydrofuran was added dropwise in 10 minutes while stirring thoroughly at a reaction temperature between 0° and 5° C. The reaction mixture was stirred for 1 hour and evaporated in vacuum. The residue was extracted with methylene chloride. The methylene chloride solution was washed with 200 ml of 0.5N sodium hydroxide solution and evaporated in vacuum. The residue was chromatographed over 500 g of silicagel using ethyl acetate as an eluent. After evaporating the good fraction, the desired ketone was obtained in a yield of 4.6 g (60%) having a melting-point of 172°-173° C.

b)
2-(Dimethylamino)-methyl-2,3,3a,4,5,6-hexahydro-1H-pyrido[3,2,1-jk]carbazol-1-one A mixture of 5.2 g (0.023 mol) of 2,3,3a,4, 5,6-hexahydro-1H-pyrido[3,2,1 jk]carbazol-1one, 4.1 g (0.05 mol) of dimethylamine hydrochloride. 1.65 g (0.055 mol) of paraformaldehyde and 70 ml of acetic acid was stirred at 100° C. for 3 hours. The mixture was then evaporated in vacuum. The residue was dissolved in methylene chloride and washed with 2N sodium hydroxide solution. The methylene chloride solution was evaporated in vacuum. The residue was chromatographed over 400 g of silicagel using methanol with 3% by volume of triethylamine as an eluent. After evaporating the desired fraction, 4.1 g (66%) of the desired Mannich base were obtained having a melting-point of 167°-169° C. (decomposition).

c)
2,3,3a,4,5,6-Hexahydro-2-[(2-methyl-1H-imidazol-1-yl)-methyl]-1H-pyrido[3,2,1jk]carbazol-1-one 3,8 g (0.014 mol) of the compound obtained sub b) were dissolved in 20 ml of boiling alcohol, 1.5 ml of concentrated hydrochloric acid were added and the mixture was evaporated, 3.3 g (0.04 mol) of 2-methylimidazole. 30 ml of 1-propanol and 30 ml of water were added to the residue. Stirring under nitrogen and at boiling temperature was then carried out for 24 hours. 30 ml of water were then added and the mixture was kept overnight at 0° C. The solid was sucked off. The mother liquor was shaken with methylene chloride, after which the methylene chloride solution was evaporated. Together with the solid already sucked off, 4.9 g of crude product were obtained. This product was chomatographed over 400 g of silicagel using methylene choride with 5% by volume of methanol as an eluent. After evaporating the desired fraction, 2.6 g (58%) of the desired product were obtained having a melting-point of 215°-216° C.

In an analogous manner were obtained:
2,3,3a,4,5,6-hexahydro-10-methoxy-2-[(2-methyl-1H-imidazol-1-yl)-methyl]-1H-pyrido[3,2,1-jk]carbazol-1-one, melting point: 169°-171° C.
2,3,3a,4,5,6-hexahydro-10-fluoro-2-[(2-methyl-1H-imidazol-1-yl)-methyl]-1H-pyrido[3,2,1-jk]carbazol-1-one, melting point: 216°-217° C.
6-[(2-methyl-1H-imidazol-1-yl)-methyl-1,2,3,3a,4,5,6,7-octahydro-benzo[b]cyclohepta[hi]indolizin-7-one hydrochloride, melting point: 225°-227° C.
3-(2-methyl-1H-imidazol-1-yl)-1-(6,7,8,9-tetrahydropyrido[1,2-a]indol-10-yl)-propanone1, melting point: 163°-164° C.

EXAMPLE II 2,3,3a,4,5,6-hexahydro-2-[(5-methyl-1H-imidazol-4-yl)-methyl]-1H-pyrido[3,2,1-jk]carbazol-1-one 6.88 mmol butyllium in hexane (4.3 ml; 1.6M) were added dropwise at −78° C. to a solution of 1.2 ml (6.88 mmol) of 2,2,6,6-tetramethylpyridine in 14 ml of dry tetrahydrofuran. The mixture was then stirred for 30 minutes at 0° C., cooled to −70° C., and added dropwise to a solution of 1-4 g (6.23 mmol) of 2,3,3a,4,5,6-hexahydro-1H-pyrido[3,2,1-jk]carbazol-1-one in 42 ml of dry tetrahydrofuran. The mixture was stirred for 90 minutes under nitrogen at −70° C. A solution of 2.4 g (6.88 mmol) of 1-triphenylmethyl-5-methyl-1H-imidazole-4-carboxaldehyde in 14 ml of dry tetrahydrofuran was then added dropwise to the reaction mixture at −70° C., and the mixture was stirred for 2 hours at −10° C. The mixture was then cooled to −70° C. and 16.8 ml of acetic acid was added dropwise. After the temperature had raised to −10° C., 8.1 g of p-toluenesulfonic acid hydrate were added. This mixture was boiled for 18 hours and evaporated in vacuum. The residue was shaken with methylene chloride and with 2N sodium hydroxide. The organic layer was separated, washed with brine, dried and evaporated. The residue was chromatographed over silicagel using methylene chloride/methanol/ammonia (92.5/7/0.5) as an eluent. 1.2 g (60%) of 2,3,3a,4,5,6-hexahydro-2-[(5-methyl-1H-imidazol-4-yl)-methylene]-1H- pyrido[3,2,1jk]carbazol-1-one were obtained. This product dissolved in 100 ml of ethanol and hydrogenated at room temperature at 1 atmosphere with palladium on carbon as a catalyst. The catalyst was removed by filtration after disappearance of the starting material, the filtrate was evaporated in vacuum, and the residue was purified by flash chromatography over silicagel using methyene chloride/methanol/ammonia (92.5/7/0.5) as an eluent. 0.49 g of the desired compound were obtained after evaporating the desired fractions.

Melting point: 289°-290° C.; $^{13}$C NMR (CDCl$_3$, Ref. TMS, additive: CD$_3$OD):

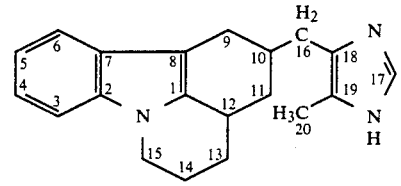

| 1 | 154.93 S    | 8  | 110.61 S | 15 | 42.18 T  |
| 2 | 137.81 S    | 9  | 195.85 S | 16 | 25.19 T  |
| 3 | 109.94 D    | 10 | 48.43 D  | 17 | 133.18 D |
| 4 | 123.31 D #  | 11 | 26.60 T  | 18 | 127.82   |
| 5 | 121.38 D #  | 12 | 33.94 D  | 19 | 129.32   |
| 6 | 123.31 D #  | 13 | 37.41 T  | 20 | 11.02 Q  |
| 7 | 125.34 S    | 14 | 22.72 T  |    |          |

BROAD LINES FOR CARBON ATOMS 18 AND 19!

We claim:
1. Compounds of formula (2):

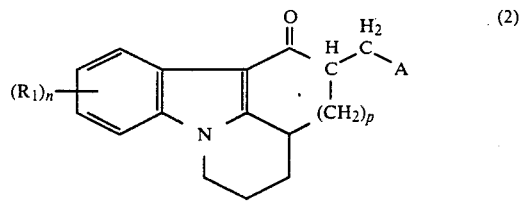

wherein
R$_1$ is alkyl or alkoxy having 1–4 C-atoms, hydroxy, halogen, trifluoromethyl, a group R$_5$R$_6$N or R$_5$R$_6$—N—CO, wherein R$_5$ and R$_6$ are hydrogen or alkyl having 1–4 C-atoms or wherein R$_5$R$_6$N is a saturated 5–6 membered ring, and n has the value 0, 1 or 2;
A is a group of formula 3, 4 or 5

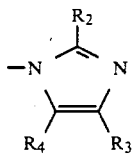 (3)

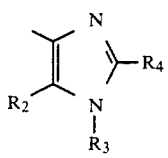 (4)

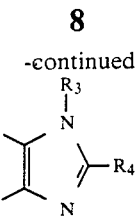 (5)

wherein one of the groups $R_2$, $R_3$ and $R_4$ is hydrogen, alkyl having 1-4 C-atoms, cycloalkyl having 3-6 C-atoms or alkenyl having 2-4 C-atoms and the two other groups, independently of each other, are hydrogen or alkyl having 1-4 C-atoms, has the value 0-3, and pharmaceutically acceptable acid addition salts thereof.

2. Pharmaceutical compositions useful as antagonists of neuronal 5-hydroxytryptamine receptors, and which comprise at least one compound as claimed in claim 1 as an active substance.

3. A method of preparing pharmaceutical compositions wherein as active ingredient a compound of formula (2) as defined in claim 1, or a pharmaceutically acceptable acid addition salt thereof, is admixed with a solid or liquid carrier.

* * * * *

UNITED STATES PATENT AND TRADEMARK OFFICE
CERTIFICATE OF CORRECTION

PATENT NO. : 5,049,563
DATED : September 17, 1991
INVENTOR(S) : Hans H. HAECK et al It is certified that error appears in the above-identified patent and that said Letters Patent is hereby corrected as shown below:

Column 6, first structural formula, in position 9 there should be shown a double-bonded oxygen atom ( $\overset{O}{\|}$ ) attached to the 9-carbon atom -- exactly as shown in the second structural formula in that same column.

Signed and Sealed this

Twenty-seventh Day of April, 1993

Attest:

MICHAEL K. KIRK

Attesting Officer

Acting Commissioner of Patents and Trademarks